(12) United States Patent
Moody

(10) Patent No.: US 6,294,589 B1
(45) Date of Patent: Sep. 25, 2001

(54) POLYURETHANE COMPOSITION CONTAINING ANTIMICROBIAL AGENTS AND METHODS FOR USE THEREFOR

(75) Inventor: Von L. Moody, Brewton, AL (US)

(73) Assignee: Shaw Industries, Inc., Dalton, GA (US)

(*) Notice: Subject to any disclaimer, the term of this patent is extended or adjusted under 35 U.S.C. 154(b) by 0 days.

(21) Appl. No.: 09/570,474

(22) Filed: May 12, 2000

(51) Int. Cl.[7] ....................................... C08J 9/00
(52) U.S. Cl. ........................... 521/76; 521/103; 521/121; 521/123; 521/124; 521/125; 521/129; 521/130; 428/355 N
(58) Field of Search ..................... 521/130, 103, 521/104, 105, 120, 121, 123, 124, 125, 128, 129, 76; 524/701, 724, 714, 742, 773, 781, 783, 784; 428/355 N

(56) References Cited

U.S. PATENT DOCUMENTS

| 4,608,289 | * | 8/1986 | McIntosh | 428/95 |
| 4,686,239 | * | 8/1987 | Rei | 521/55 |
| 5,114,984 | | 5/1992 | Branch et al. | . |
| 5,319,000 | | 6/1994 | O'Connor et al. | . |
| 5,639,803 | | 6/1997 | Anderson et al. | 523/122 |
| 6,150,489 | * | 11/2000 | Pudleiner et al. | 528/49 |

OTHER PUBLICATIONS

D'Ruiz, Carl MPH, "Treated Articles: Going, Going, Gone?," Presentation dated Nov. 12, 1998 by Carl D'Ruiz, Exec. Director, Product Stewardship and Regulatory Affairs, Ciba.

Simpson, D., "Dry Film Protection for Advanced Adhesive Systems," Reprinted from *Adhesive Technology* (Jun. 1998).

Olin Biocides Brochure (1998).

Culleen, Lawrence E., "The War on Germs (and GermFighting Products) Heats Up," The Bureau of National Affairs, Inc., *Chemical Regulation Reporter*, 21(34) (Nov. 21, 1997).

AATCC Test Method 174–1993,"Antimicrobial Activity Assessment of Carpets," *AATCC Technical Manual*, pp. 319–322 (1996).

Herrington, R., et al., "Chapter 5: Flexible Foam Preparation," *Flexible Polyurethane Foams*, Publisher: Unknown, Publication Date: Unknown.

Skaggs, K., et al., "Chapter 10: Carpet Backing," *Flexible Polyurethane Foams*, Publisher: Unknown, Publication Date: Unknown.

* cited by examiner

Primary Examiner—James J. Seidleck
Assistant Examiner—Melanie D. Bagwell
(74) Attorney, Agent, or Firm—Needle & Rosenberg, P.C.

(57) ABSTRACT

A polyurethane composition for fabricating antimicrobial based products such as polyurethane foam carpet backing materials and carpets having a polyurethane foam carpet backing material. The polyurethane composition includes a plurality of particles comprising an antimicrobial agent which are at least partially encapsulated by a plasticizer material before being dispersed within a polyurethane.

23 Claims, No Drawings

POLYURETHANE COMPOSITION CONTAINING ANTIMICROBIAL AGENTS AND METHODS FOR USE THEREFOR

BACKGROUND OF THE INVENTION

1. Field of Invention

The present invention relates to a polyurethane composition and methods for use of a polyurethane composition. More particularly, the present invention relates to a polyurethane composition having antimicrobial properties, and to methods for fabricating this composition for use in commercial settings, such as in a backing materials or padding for carpeting used hospitals and schools.

2. Background Art

In the floor covering industry, it is well-known that the installation of vinyl, tile or carpet provides microorganisms such as bacteria and fungi with a fertile environment for growth as the adhesives and the polymers used to manufacture the floor covering provide the organisms with abundant carbonaceous food sources. Where such floor coverings are applied over a padding and/or over highly alkaline surfaces, such as fresh cement sub-flooring, the microorganisms are provided with an even more favorable environment for growth. Over time, the effects of microorganism proliferation are manifested by a loss in the physical and/or aesthetic qualities of the flooring product and/or padding. In some instances, the effects are manifested by discoloration of the flooring product. In others, the effects are manifested by deterioration of the padding itself or of the adhesive backing to the extent that the adhesive no longer provides adhesion of the flooring product to the substrate surface. In still others, the effects are manifested by a combination of these conditions. The impact of these circumstances is most strongly felt in the carpet industry where carpet products and padding materials are used in commercial as well as residential, outdoor settings and in commercial and non-commercial vehicles.

Carpeting basically consists of a backing material having a carpet pile on one side of it. Carpet manufacturers, and more particularly tufted carpet manufacturers, typically use a binding material to attach a secondary backing material which could be a foam backing composition to complete the carpet product. The binding material that adheres secondary backing materials typically consists of a latex based adhesive that locks the carpet tufts to the backing material. The foam backing composition typically consists of a PVC plastisol, polyurethanes, EVA or latex that creates a cushion which increases walking comfort and enables a reduction in the amount of carpet pile used to create the carpet's cushion. Carpet padding is typically fabricated from materials similar to those used for foam backing compositions.

Polyurethanes are typically preferred for the formation of the secondary backing material as, though more expensive than latex, they provide product advantages which allow the carpet to maintain its appearance and backing integrity. These advantages notwithstanding, carpet manufacturers have experienced difficulty in using polyurethanes in backing material fabrication where attempts have been made to incorporate an antimicrobial agent into the backing material. Some antimicrobial agents are solids in their naturally occurring state and, as such, are difficult to manipulate. In a dry state, the chemical properties of the agents can disrupt the catalytic reaction required for formation of the polyurethanes. Accordingly, it has been difficult, if not impossible, to effectively incorporate dry antimicrobial agents into the polyurethane foam backing material used to fabricate the carpet products and carpet padding that is manufactured and sold.

The art has looked to liquids for incorporating an antimicrobial agent into polyurethane compounds. One such method incorporates an arsenic based antimicrobial agent, such as OBPA or vinyzene, dispersed in a glycol, to form a polyurethane product. Still other methods and products known in the art are disclosed in U.S. Pat. No. 5,114,984 issued to Branch, et al. ("the '984 patent"); U.S. Pat. No. 5,319, 000 issued to O'Connor, et al.("the '000 patent"); and, U.S. Pat. No. 5,639,803 issued to Anderson, et al. ("the '803 patent").

The '984 patent discloses a method for producing an antimicrobial polyurethane foam product wherein the biocide is liquified in the formation of the foam product. The '803 patent discloses a method for liquefying a biocide to form a preliminary dispersion which must then be heated to an elevated temperature and cooled to form the claimed dispersion. The '000 patent provides a method for forming a biocide by combining it with a non-polyurethane plastisol prior to heating and cooling the foam product in a manner similar to that described in the '803 patent.

Each of the methods disclosed in these patents requires the use of water to complete the liquefaction step and produce polyurethane foam product. The use of water to produce the polyurethane product formed by these methods compels the use of more isocyanate to combine with the polyol in mixture and insure completeness of the polyurethane forming reaction. Moreover, at least one of these methods also requires the addition of other chemicals to insure that the biocide remains suspended in the liquid dispersion so that it may be stored over an extended period of time.

SUMMARY OF THE INVENTION

The present invention is based, at least in part, on the surprising discovery that encapsulating an antimicrobial agent can aid in maintaining its effectiveness in polyurethane compositions.

The polyurethane composition of the present invention can include a plurality of particles comprising one or more at least partially encapsulated antimicrobial agents. The polyurethane can be used to fabricate a variety of products wherein antimicrobial properties are desired, such as carpeting and backing materials for carpet products.

Another aspect of this invention relates to a method for producing the polyurethane that includes the steps of at least partially encapsulating a plurality of particles comprising one or more antimicrobial agent(s) and introducing the at least partially encapsulated antimicrobial agents into the polyurethane. The method is preferably performed by introducing the agent(s) into at least one of either the components used to fabricate the polyurethane or the mixer into which the components are combined to create the polyurethane.

The polyurethane can then be employed in a desired manner. For example, in making a carpet backing material or related carpet product, the method can further include the step of incorporating the compound within that carpeting material.

PREFERRED EMBODIMENTS OF THE INVENTION

The present invention relates to a polyurethane composition, at least one method for producing of a polyurethane composition, and at least one method for using a polyurethane in the manufacture of a floor covering, such as a carpet. As those skilled in the art will readily recognize, the use this polyurethane composition in producing a microorganism resistant floor covering such as carpet is but one example of the applicability of this composition and is not in any way intended to otherwise limit the scope of the applicability of this polyurethane composition.

Antimicrobial agents can be effective in combating microbial infestation in a variety of different industries and in a variety of different applications within those industries. Included within the scope of these applications is the use of antimicrobial agents in architectural and marine paints and coatings, in metal working lubricants and coolants, in personal hygiene products such as dandruff shampoos, and in flooring and wall coverings, generally.

The antimicrobial agent(s) suitable for use in the invention include any agent effective against a microorganism such as bacteria, algae, fungus, and the like. Agents preferred for use in production of the polyurethane composition of the present invention is also free of volatile organic compounds. Thus, its use will not contribute volatile organic components to the product during its manufacture or ultimate use. Moreover, the antimicrobial agent preferred for use with the present invention has a favorable toxicological and environmental profile and is effective against both gram positive and gram negative bacteria, and fungi. Finally, the methods for production of the antimicrobial polyurethane composition of the present invention are less expensive and less complicated than any other methods heretofore known or used in the art.

Antimicrobial agents available for incorporation into the polyurethane composition of the present invention also depend on the intended use of the polyurethane composition. The antimicrobial agent used in the present invention include both discrete compounds which guard against a particular type of microbial growth, or of a combination of agents which work in combination to provide a broader range of protection against a wider scope of microorganisms. To this end, suitable antimicrobial agents include those antimicrobial powders known in the art. Specific examples include but are not limited to diphenyl antimony, ethylhexoate, tetramethylthiuram disulfide, zinc dimethyldithiocarbamate, zinc oxide, dithiopyridine dioxide, copper naphthenate, doddecyldimethyl benzylammonium naphthenate, dibromosalicylanilide, barium metaborate, tributyl tin oxide,2-n-octyl-4-isothiazolin-3-one, triclosan, and pyrithione, among which are zinc, sodium and copper pyrithione. Such agents are effective in combating or defeating the proliferation of most common types of microorganisms, including fungi, algae and bacteria.

The present invention can include both commercially and non-commercially prepared antimicrobial agents. Where non-commercially prepared antimicrobial agents are used, it is preferred that they meet the standards for antimicrobial activity set forth in 1996 AATCC Technical Manual publication entitled "Antimicrobial Activity Assessment of Carpets." Where commercially prepared antimicrobial agents are employed, pyrithiones, and more particularly zinc and sodium pyrithiones are most preferred. Zinc and sodium pyrithione are most effective in protecting against growth fungi, algae and/or bacteria.

Arch Chemicals, Inc. is one of several major chemical manufacturer that manufactures zinc pyrithione and sodium pyrithione. Arch markets its products under the names zinc Omadine® and sodium Omadine®, respectively. The description of the present invention, and the following Examples, contemplate the use of Arch products in present invention. Those skilled in the art will recognize, however, that the description of the Arch products herein is exemplary only and is not intended to limit the scope of the present invention in any manner. Moreover, while it will be recognized that use of zinc pyrithione is preferred in the formulation of the antimicrobial polyurethane of the present invention, it should also be recognized that sodium pyrithione may be used in certain applications of the present invention.

As is frequently the case in industry, the optimum concentration of product components combined to produce the product are a function of the cost to manufacture the product and the amount of the component needed to make the product efficacious. As illustrated in the Examples, where zinc pyrithione is employed in antimicrobial polyurethane compositions for industrial carpet backing materials, for example, effective inhibition of microbial growth is attained where the antimicrobial agent is used in concentrations of at least 1000, and more preferably, at least 2000ppm. Though not shown in the Examples, effective inhibition of microbial growth for non-commercial or non-industrial carpet backing materials is attained where the concentration of the agent used is approximately at least 4000ppm. As those skilled in the art will recognize, the concentration of antimicrobial agent dispersed in the polyurethane of the present invention will vary depending on the type of antimicrobial agent being used and the particular application in which it is used.

The antimicrobial polyurethane composition of the present invention includes a plurality of particles comprising an antimicrobial agent dispersed in and at least partially encapsulated by a plasticizer material. The partially encapsulated antimicrobial agent can be inserted into a precursor component used to fabricate the polyurethane or into the mixer into which the components are combined to create the antimicrobial polyurethane composition.

Plasticizers, which are known in the art, primarily relate to esters based on alcohols and organic acids. Those skilled in the art will recognize that the choice of a particular plasticizer agent is dependent on the intended use of the composition. Examples of plasticizers include diphenyl and triphenyl phosphates and toluensulfonamides, such as are manufactured by Akzo Nobel, and phthalates, adipates and aliphatic dicarboxylic acids, such as are manufactured by BASF, and as are marketed their respective company trade names. Of these plasticizer agents, phthalate-based plasticizer materials are preferred as they are the most effective for use in producing antimicrobial polyurethane of the present invention. A specific example of a plasticizer suitable for use in the present invention is diisodecyl phthalate.

A method for fabricating the antimicrobial polyurethane composition of the present invention includes the steps of at least partially encapsulating a plurality of particles comprising an antimicrobial agent with plasticizer material and dispersing the at least partially encapsulated antimicrobial agent into at least one of either the polyurethane fabricating components or into the mixer into which those components are combined to create the polyurethane product.

Encapsulation methods such as those suitable for use in the present invention are generally known in the art. These methods include, but are not limited to processes in which the substance to be encapsulated is dispersed into the encapsulating fluid and those in which the substance to be encapsulated is immersed by the encapsulating fluid.

The antimicrobial polyurethane composition of the present invention may be used to form polyurethane foam products of any density. As is known to those skilled in the art, polyurethane foam density is a measure of the amount of air or filler in the foam product. Polyurethane foam products having a density of 2–8 pounds per cubic foot are commonly known as light polyurethanes, and are typically used in residential or non-commercial settings. Polyurethane foam products having a density of 18–24 pounds per cubic foot are commonly known as dense polyurethanes, and are typically used in commercial settings. While any polyurethane can be employed, in the preferred embodiment, the floor covering of the present invention is a dense antimicrobial polyurethane composition suitable for commercial applications such as in healthcare institutions and educational facilities where there is normally a high risk for exposure to infective microorganisms.

Methods for the formation of polyurethanes are recognized in the art. These methods include, but are not limited to the reaction of a polyol compound and an isocyanate compound to form the polyurethane. Any recognized combination of polyol and isocyanate can be used with the present invention. Dow Chemical, for example, manufactures isocyanates, such as Isonate®, and polyols, such as Voranol®, which are compatible for use in the present invention. The reaction to form the polyurethane can be initiated by a polyurethane catalyst. For example, the catalyst can be inserted into the polyol compound separately to initiate the reaction or be included in the polyol as part of a polyol compound that is ready made for mixing with the isocyanate. Still other methods for the formation of polyurethane will be known to those skilled in the art.

The antimicrobial agent may be introduced at any point before, during, or after formation of the polyurethane. It is preferred that the agent be introduced into a precursor, i.e., the polyol or the isocyanate, of the polyurethane.

Depending on the physical properties desired, one or more additives including, but not limited to, calcium carbonate, aluminum trihydrate, silicone and pigment can also be incorporated into the carpet product.

In a first embodiment of the present invention, the antimicrobial polyurethane composition is a dense polyurethane which is employed in a method for manufacturing an underlayment or a foam backing material having antimicrobial properties. In this embodiment, the polyurethane is fabricated by combining a polyol compound and with an isocyanate. According to a preferred method for fabricating the antimicrobial polyurethane composition of the present invention, zinc pyrithione is first dispersed into a diisodecyl phthalate-DIDP solution to encapsulate the pyrithione antimicrobial agent and the diisodecyl phthalate-DIDP encapsulated pyrithione agent is then dispersed into one of either the polyol compound or the isocyanate or the mixer into which these components are combined to create the polyurethane product. A high density foam polyurethane is then formed by using a gas such as air or nitrogen to form the foam polyurethane. Dispersion of the antimicrobial agent into the plasticizer material prior to its combination in either of the polyurethane components or the polyurethane is preferred, according to the present invention, as the encapsulation of the agent within the plasticizer isolates it from reacting with the catalyst and prevents it from interfering with the polyurethane formation reaction.

In a second embodiment, the antimicrobial polyurethane composition of the present invention is employed in a method for fabricating a carpet product, and in particular, a tufted carpet product, having antimicrobial properties. In an example of this embodiment, the carpet product includes a primary backing material having a front surface and a rear surface, at least one loop of yarn secured to the primary backing material to create a carpet surface extending from the front surface of the primary backing material and a backing material contacted with the primary backing material for substantially penetrating and consolidating the at least one loop of yarn. In this embodiment, the backing material can comprise the antimicrobial polyurethane composition which is fabricated according to the methods described above. The carpet surface is fabricated by any method known in the art, including but not limited to, tufting the at least one loop of yarn onto the primary backing material. The method of this embodiment further includes the step of applying the adhesive backing material to the rear surface of the primary backing material.

The polyurethane of the present invention can solve the problems manifested by polyurethanes compounds heretofore known in the art by at least partially encapsulating the desired agent(s) prior to being introduced into the polyurethane. Encapsulation of the antimicrobial agent can further eliminate the handling difficulties heretofore experienced by those skilled in the art, such as the unintended airborne dispersion of the agent, for example. Encapsulation of the antimicrobial agent can further insulate the agent from interfering with the reactant used in forming the polyurethane. It can also eliminate the need for water and/or liquefaction of the antimicrobial agent prior to its addition to either the components of or the mixture comprising the polyurethane product. Moreover, encapsulation does not interfere with the agent's antimicrobial effectiveness, e.g., in combating the growth of the gram positive or the gram negative bacteria or fungi that typically destroy the resilient foam carpet backing or backing materials used with carpets heretofore known manufactured in the art. The polyurethane of the present invention can also be more durable for the end use consumer as its low water solubility reduces, if not eliminates, the possibility that the agent will leach out of the polyurethane, even after repeated exposure to water.

The present invention will now be described in connection with certain examples thereof. These examples are illustrative in nature and should in no way limit the scope of the present invention.

EXAMPLES

Example 1

Table I illustrates data collected when a zinc Omadine®-based antimicrobial polyurethane was first submitted for microbiological testing. In this analysis, zinc Omadine® containing samples were placed in intimate contact with nutrient that was previously streaked with a bacterial culture. *Staphylococcus aureus* and *klebsiella pneumoniae* were the representative bacteria used for the study. According to the test criteria employed, to constitute acceptable antibacterial activity, there must have been no bacterial colonies growing under the sample in the contact area. After incubation, a clear area of interrupted growth underneath and along the sides of the test material indicated antibacterial activity by the specimen. As indicated in Table I, in the control sample, no growth inhibition was observed underneath the sample as the sample lacked the materials necessary to inhibit or control bacterial growth. Where 1000 ppm of zinc Omadine® was dispersed in a sample, growth of *staphylococcus aureus* bacteria was inhibited over an area between 5.5 to 7.0 mm in diameter and growth of *klebsiella pneumoniae* was inhibited over an area between 7.0 to 10.0 mm in diameter. Where 2000 ppm of zinc Omadine® was dispersed in a sample, growth of the *staphylococcus aureus* bacteria was inhibited over an area between 7.5 to 9.0 mm in diameter and growth of *klebsiella pneumoniae* was inhibited over in an area approximately 13.0 mm in diameter. The zinc Omadine®-based antimicrobial polyurethane exhibited similar efficacy in testing on antifungal applications, as well. The polyurethane preferably used in these applications is a thermoset material. Those skilled in the art will recognize that other concentrations of zinc Omadine® and other phthalate-based plasticizer materials are adaptable for use in the antimicrobial polyurethane composition of the present invention, depending on its application.

EXAMPLE 2

Tables IIA–IIC illustrates data collected when a zinc Omadine®-based antimicrobial polyurethane was first submitted for follow-up microbiological testing. The object of this analysis was to define the antimicrobial performance of the zinc Omadine®-based antimicrobial polyurethane. The test included a qualitative and a quantitative assessment of antibacterial activity and a qualitative antifungal test.

In the qualitative antibacterial assessment, specimens are placed in contact with nutrient agar that was previously streaked with a bacterial culture. After incubation, a clear area of uninterrupted growth underneath and along the sides of the test material indicates antibacterial activity by the specimen. *Staphylococcus aureus* and *Klebsiella pneumoniae* are the representative bacteria. A zone of inhibition, if present, is measured and reported in millimeters in Table IIA. Growth beneath the sample, if present, is also noted in Table IIA.

In the quantitative antibacterial assessment, specimens are inoculated with test organisms *Staphylococcus aureus* and *Klebsiella pneumoniae*. After incubation at 37° C. for 24 hours, bacteria eluted from swatches following an immersion in known amounts of liquid. The number of bacteria present in this liquid is determined and bacterial counts are reported as the number of bacteria per specimen. The bacterial reduction is calculated by a formula that considers the number of bacteria recovered immediately after inoculation relative to the number of bacteria recovered after inoculation and incubation. Bacterial counts are calculated and reported for washed and unwashed specimens. The data accumulated are reported in Table IIB.

In the qualitative antifungal assessment, carpet is subjected to the growth of a common fungus, *Aspergillus niger*, on a nutrient agar medium. Pre-wet specimens are inoculated and incubated at 28° C. for seven days. Carpet specimens are inoculated with fibers up and with the fibers down in separate petri dishes. Fibers and backing are then assessed for growth on the specimen. A zone of inhibition, if present, is measured and reported in millimeters in Table IIC. Microscopic and macroscopic growth on the specimen is also reported in Table IIC. Assessments are also made for washed and unwashed specimens.

It will be apparent to those skilled in the art that many modifications, additions, and deletions can be made to the present invention without departing from the spirit and scope of the invention and its equivalents as set forth in the following claims.

TABLE I

| Poly- | Biocide | Zone of Inhibition (mm) | |
| --- | --- | --- | --- |
| urethane Sample | Use Level (ppm) | *Staphylococcus aureus* ATCC 6538 | *Klebsiella pneumoniae* ATCC 4352 |
| Control | 0 | NZ/GCA, NZ/GCA | NZ/GCA, NZ/GCA |
| 6G | 1000 ppm | 5.5/NGCA, 7.0/NGCA | 10.0/NGCA, 7.0/NGCA |
| 12G | 2000 ppm | 7.5/NGCA, 9.0/NGCA | 13.0/NGCA, 13.0/NGCA |

Key
NZ = No Zone of Inhibition
GCA = Growth in Contact Area (directly beneath sample)
NGCA = No Growth in Contact Area
4.5/NGCA = A Zone of Inhibition 4.5 mm in Diameter/No Growth Contact Area

TABLE IIA

| zinc | | | Zone of Inhibition (mm) | |
| --- | --- | --- | --- | --- |
| Omadine ® | Treatment | Surface | *Staphylococcus aureus* | *Klebsiella pneumoniae* |
| 0 | Unwashed | Backing | NZ/NGCA, NZ/NGCA | NZ/NGCA, NZ/NGCA |
| 0 | Washed | Backing | NZ/NGCA, NZ/NGCA | NZ/NGCA, NZ/NGCA |
| 1000 | Unwashed | Backing | 7.0/NGCA, 7.5/NGCA | 9.0/NGCA, 9.0/NGCA |
| 1000 | Washed | Backing | 8.5/NGCA, 9.0/NGCA | 10.0/NGCA, 11.0/NGCA |
| 2000 | Unwashed | Backing | 7.5/NGCA, 7.5/NGCA | 8.0/NGCA, 8.5/NGCA |
| 2000 | Washed | Backing | 8.0/NGCA, 8.5/NGCA | 9.0/NGCA, 9.0/NGCA |

Key
NZ/GCA = No Zone of Inhibition/Growth Contact Area (directly under sample)
NZ/NGCA = No Zone of Inhibition/No Growth in Contact Area
7.0/NGCA = A Zone of Inhibition 7.0 mm in diameter/No Growth Contact Area
7.0/NGCA, 7.0/NGCA = A Zone of Inhibition 7.0 mm in diameter on two replicates

TABLE IIB

| (ppm) zinc Omadine ® | Treatment | Surface | Staphylococcus aureus | | | Klebsiella pneumoniae | | |
|---|---|---|---|---|---|---|---|---|
| | | | 0 Hour CFU/ Sample | 24 Hour CFU/ Sample | % Reduction | 0 Hour CFU/ Sample | 24 Hour CFU/ Sample | % Reduction |
| 0 | Unwashed | Backing | $5.9 \times 10^4$ | $1.0 \times 10^6$ | *NR | $5.0 \times 10^4$ | $>3.0 \times 10^6$ | *NR |
| 0 | Washed | Backing | $1.2 \times 10^5$ | $<10^2$ | >99.9 | $7.2 \times 10^4$ | $>3.0 \times 10^6$ | *NR |
| 1000 | Unwashed | Backing | $4.9 \times 10^4$ | $6.0 \times 10^4$ | *NR | $6.0 \times 10^4$ | $1.0 \times 10^6$ | *NR |
| 1000 | Washed | Backing | $9.2 \times 10^4$ | $3.1 \times 10^4$ | 66.3 | $7.4 \times 10^4$ | $2.0 \times 10^2$ | 99.7 |
| 2000 | Unwashed | Backing | $8.6 \times 10^4$ | $7.5 \times 10^2$ | 99.1 | $7.7 \times 10^4$ | $1.0 \times 10^6$ | *NR |
| 2000 | Washed | Backing | $9.2 \times 10^4$ | $5.0 \times 10^2$ | 99.5 | $7.8 \times 10^4$ | $1.0 \times 10^6$ | *NR |

Key
*NR = No Reduction in Bacterial Count

TABLE IIC

| zinc Omadine ® | Treatment | Growth Rate | Backing Zone of Inhibition |
|---|---|---|---|
| 0 | Unwashed | 0,0 | No Zone of Inhibition |
| 0 | Washed | 0,0 | No Zone of Inhibition |
| 1000 | Unwashed | 0,0 | No Zone of Inhibition |
| 1000 | Washed | 0,0 | No Zone of Inhibition |
| 2000 | Unwashed | 0,0 | No Zone of Inhibition |
| 2000 | Washed | 0,0 | No Zone of Inhibition |

Key
0,0 = No growth on two replicates

What is claimed is:

1. A polyurethane composition containing antimicrobial agent(s) comprising:
   a plurality of particles comprising one or more antimicrobial agents, said antimicrobial agents being at least partially encapsulated by a plasticizer material; and
   a polyurethane foam, said at least partially encapsulated antimicrobial particles being dispersed within said polyurethane foam.

2. The polyurethane composition of claim 1 wherein the polyurethane composition is a dense polyurethane foam.

3. The polyurethane composition of claim 1 wherein the antimicrobial agent is selected from the group consisting of diphenyl antimony, ethylhexoate, zinc dimethyldithiocarbamate, zinc oxide, tetramethylthiuram disulfide, dithiopyridine dioxide, doddecyldimethyl benzylammonium naphthenate, dibromosalicylanilide, barium metaborate, copper naphthenate, tributyl tin oxide, 2-n-octyl-4-isothiazolin-3-one, triclosan, sodium pyrithione and zinc pyrithione.

4. The polyurethane of claim 1 wherein the plasticizer material is a phthalate-based material.

5. The polyurethane of claim 4 wherein the phthalate-based material is diisodecyl phthalate-DIDP.

6. A method for fabricating a foam polyurethane composition comprising:
   a) at least partially encapsulating one or more particles comprising one or more antimicrobial agents;
   b) dispersing the at least partially encapsulated particles into at least one precursor for a foam polyurethane; and
   c) forming a foam polyurethane so as to provide a composition containing the at least partially encapsulated antimicrobial particles.

7. The method of claim 6 wherein the polyurethane is formed by a reaction of at least two components and the particles of the at least partially encapsulated antimicrobial agent are dispersed within at least one of the components before forming the polyurethane.

8. The method of claim 7 wherein the polyurethane compound is formed by a combination of a polyol compound and isocyanate.

9. The method of claim 6 wherein the antimicrobial agent is selected from the group consisting of diphenyl antimony, ethylhexoate, zinc oxide, zinc dimethyldithiocarbamate, tetramethylthiuram disulfide, dithiopyridine dioxide, doddecyldimethyl benzylammonium naphthenate, dibromosalicylanilide, barium metaborate, copper naphthenate, tributyl tin oxide, 2-n-octyl4-isothiazolin-3-one, triclosan, sodium pyrithione and zinc pyrithione.

10. The method of claim 6 wherein the plasticizer material is a phthalate-based material.

11. The method of claim 10 wherein the phthalate-based material is diisodecyl phthalate-DIDP.

12. The method of claim 6 wherein the polyurethane compound is formed by a reaction of at least two components and the antimicrobial agent containing plasticizer material is dispersed when the at least two components are reacted.

13. The method of claim 12 wherein the polyurethane compound is formed by a reaction of a polyol compound and isocyanate.

14. A method for fabricating a carpet product having antimicrobial properties, the carpet product comprising a primary backing material having a front surface and a rear surface and an adhesive comprising a foam polyurethane in contact with the primary backing material, the method comprising:
   a. at least partially encapsulating a plurality of particles comprising one or more antimicrobial agents with a plasticizer material to form at least partially encapsulated antimicrobial particles;
   b. dispersing the at least partially encapsulated antimicrobial agents into a foam polyurethane precursor; and
   c. applying the adhesive to the rear surface of the primary backing material.

15. The method of claim 14 wherein the adhesive backing material is a dense polyurethane.

16. The method of claim 14 wherein the antimicrobial agent is selected from the group consisting of diphenyl antimony, ethylhexoate, zinc oxide, zinc dimethyldithiocarbamate, tetramethylthiuram disulfide, dithiopyridine dioxide, doddecyldimethyl benzylammonium naphthenate, dibromosalicylanilide, barium metaborate, copper naphthenate, tributyl tin oxide, 2-n-octyl-4-isothiazolin-3-one, triclosan, sodium pyrithione and zinc pyrithione.

17. The method of claim 14 wherein the plasticizer material is a phthalate-based material.

18. The method of claim 17 wherein the phthalate-based material is diisodecyl phthalate-DIDP.

19. An adhesive material for a carpet having antimicrobial properties comprising:
- a plurality of particles comprising one or more antimicrobial agents, said antimicrobial agents being at least partially encapsulated by a plasticizer material; and
- a polyurethane foam suitable for use as an adhesive, said at least partially encapsulated antimicrobial agent being dispersed within said polyurethane foam.

20. The adhesive material of claim 19 wherein the polyurethane compound is a dense foam polyurethane.

21. The adhesive material of claim 19 wherein the antimicrobial agent is selected from the group consisting of diphenyl antimony, ethylhexoate, zinc oxide, zinc dimethyldithiocarbamate, tetramethylthiuram disulfide, dithiopyridine dioxide, doddecyldimethyl benzylammonium naphthenate, dibromosalicylanilide, barium metaborate, copper naphthenate, tributyl tin oxide,2-n-octyl-4-isothiazolin-3-one, triclosan, sodium pyrithione and zinc pyrithione.

22. The adhesive material of claim 19 wherein the plasticizer material is a phthalate-based material.

23. The adhesive material of claim 22 wherein the phthalate-based material is diisodecyl phthalate-DIDP.

* * * * *